(12) United States Patent
Zemmouri et al.

(10) Patent No.: US 8,585,688 B2
(45) Date of Patent: Nov. 19, 2013

(54) COOLED HANDPIECE FOR TREATING THE SKIN WITH VISIBLE RADIATION

(75) Inventors: Jaouad Zemmouri, Genech (FR); Jean Ringot, Mons en Baroeul (FR); Mohammed Zemmouri, Lille (FR)

(73) Assignee: LSO Medical, Loos (FR)

( * ) Notice: Subject to any disclaimer, the term of this patent is extended or adjusted under 35 U.S.C. 154(b) by 496 days.

(21) Appl. No.: 12/672,966

(22) PCT Filed: Aug. 5, 2008

(86) PCT No.: PCT/FR2008/001170
§ 371 (c)(1), (2), (4) Date: Feb. 10, 2010

(87) PCT Pub. No.: WO2009/056690
PCT Pub. Date: May 7, 2009

(65) Prior Publication Data
US 2011/0184396 A1    Jul. 28, 2011

(30) Foreign Application Priority Data
Aug. 16, 2007 (FR) ..................................... 07 05859

(51) Int. Cl.
*A61B 18/18*    (2006.01)
(52) U.S. Cl.
USPC .................................... 606/9; 606/22; 606/23
(58) Field of Classification Search
USPC ............. 606/31, 9–12, 22–24; 607/88–91, 93
See application file for complete search history.

(56) References Cited

U.S. PATENT DOCUMENTS

| | | | |
|---|---|---|---|
| 6,059,820 A | 5/2000 | Baronov | |
| 6,264,649 B1 | 7/2001 | Whitcroft et al. | |
| 6,383,176 B1 | 5/2002 | Connors et al. | |
| 6,485,484 B1 | 11/2002 | Connors et al. | |
| 6,530,920 B1 | 3/2003 | Whitcroft et al. | |
| 6,770,069 B1 * | 8/2004 | Hobart et al. ..................... | 606/9 |
| 2002/0035360 A1 | 3/2002 | Connors et al. | |
| 2002/0120315 A1 | 8/2002 | Furuno et al. | |

FOREIGN PATENT DOCUMENTS

| | | |
|---|---|---|
| EP | 0827716 | 3/1998 |
| EP | 0827716 | * 11/1998 |
| WO | WO-99/52594 | 10/1999 |
| WO | WO-00/54685 | 9/2000 |

OTHER PUBLICATIONS

Julio C. Ramirez-San-Juan, Bernard Choi, Walfre Franco, J. Stuart Nelson, and Guillermo Aguilar, "Effect of ambient humidity on light transmittance through skin phantoms during cryogen spray cooling," Physics in Medicine and Biology, 51 (2006), pp. 113-120.

* cited by examiner

*Primary Examiner* — Armando Rodriguez
(74) *Attorney, Agent, or Firm* — Harness, Dickey & Pierce, P.L.C.

(57) ABSTRACT

The handpiece for treating the skin with irradiation using a light beam (F1), comprises a first window (1) and a second window (2) and first means for cooling the first window (1). Said first window (1) and said second window (2) are positioned opposite one another and are separated by a gas-filled space. They are capable of transmitting a light beam (F1) and said first window (1) is intended to be applied in contact with the skin during the treatment. The handpiece comprises means for heating the gas between the two windows (1, 2).

37 Claims, 6 Drawing Sheets

COOLED HANDPIECE FOR TREATING THE SKIN WITH VISIBLE RADIATION

CROSS REFERENCE TO RELATED APPLICATIONS

This application is a 371 U.S. National Stage of International Application No. PCT/FR2008/001170, filed Aug. 5, 2008. This application claims the benefit of French Patent Application No. FR 0705859, filed Aug. 16, 2007. The disclosures of the above applications are incorporated herein by reference.

1. Field of the Invention

The present invention relates to a handpiece for irradiating a treatment zone, for instance the skin of a patient, with the help of a light energy source and in particular a laser source. It is principally applied in the medical field of dermatology and more particularly for vascular, depilatory or pigmentary treatments.

2. Prior Art

Handpieces are commonly used in the medical field of dermatology and more particularly in the case of vascular, depilatory and pigmentary treatments. Such handpieces are generally linked via an optical fibre to a light energy source, and in particular to a laser source, which enables a light beam to be generated, which is to be focused on a treatment zone. To this effect, the handpiece is foreseen with a window, most often made out of sapphire, suitable for letting the irradiating light beam pass through. The sapphire represents a real advantage as, besides its good optical efficiency, it features good thermal conductivity necessary for its cooling.

Indeed, in the field of dermatology and treatments of the skin of a patient using a light source such as a laser, it is often necessary to cool the skin of the patient or the element in contact with the skin of the patient. This cooling is important since, on the one hand, risks of burning caused by the laser radiation on the skin of the patient can be prevented and, on the other hand, the pain in the treatment zone can be minimised at the moment of impact of the laser shot.

This cooling of the skin or the element in contact with the skin nevertheless gives rise to a first disadvantage, namely that of the appearance of condensation on the window. The phenomenon of condensation is in particular highlighted in the publication "Effect of ambient humidity on light transmittance through skin phantoms during cryogen spray cooling" by Julio C Ramirez-San-Juan, Bernard Choi, Walfre Franco, J. Stuart Nelson and Guillermo Aguilar, Physics in Medicine and Biology, 51 (2006), pp 113-120. The condensation is detrimental to the proper carrying out of the treatment as it reduces the transmittance of the light beam and thus reduces the power of the shot. In addition, the condensation also reduces good visibility of the treatment zone and of the shot in the case of a handpiece supplied with a visualisation device such as a camera.

A second disadvantage of the handpieces supplied with a cooling device lies in their lack of compactness and the fact that they are not easy to use. Non-integrated devices, which apply a cooling gel to the skin of the patient, are not very practical and the handpieces foreseen with an integrated cryogenic spray are cumbersome.

For these reasons, a handpiece comprising a sapphire window linked to a Peltier-effect cooling device proves to be an excellent solution, since it is compact in comparison with the device using a cryogenic spray integrated with the handpiece, and is easier to use compared with the non-integrated devices that consist in applying a cold gel to the skin prior to the laser shot.

The cooling by means of a thermoelectric Peltier-effect device acts in the manner of a heat pump. More precisely, the Peltier effect is a physical phenomenon of heat displacement from a cold source to a heat source in the presence of an electric current. The device functions in the manner of a heat pump, the cold face thus becoming cool while the warm face heats up.

Such a handpiece comprising a thermoelectric cooling device is for instance described in American patent application US 2002/0120315. It comprises in particular a first sapphire window intended to make contact with the skin of the patient, a Peltier-effect cooling unit linked to the first window, and a second window made out of transparent glass covered with an aluminium cover provided with an opening. The cooling unit is subjected to temperature control means, which are linked to temperature sensors. These control means enable a first temperature to be set in order to limit condensation from forming on the sapphire window, and a second temperature to be set, lower than the first temperature, for the use of the handpiece in contact with the skin. The first window and the second window are separated by the support and thermal insulators, one of which is a closed space and the other a resin. In addition, the heat source of the thermoelectric cooling device is situated against a cooling plate in which a cooling liquid circulates.

This cooling device intended to limit the appearance of condensation is relatively efficient, but only during a short period of use. Indeed, the handpiece cannot be used for prolonged periods since the temperature of the air contained in the closed space would drop significantly, thus encouraging the appearance of condensation on the windows. Indeed, below a temperature of the air contained in the closed space between the two windows, typically for air temperatures lower than approximately 15° C., the formation of condensation on the windows is strongly encouraged.

OBJECTIVES OF THE INVENTION

The objective of the present invention is to suggest a new cooled handpiece for carrying out dermatological treatment via irradiation by means of a light beam. This new handpiece, even in the case of prolonged use, has the advantage of strongly limiting the appearance of condensation on the window, which is cooled and intended to come into contact with the skin of the patient.

SUMMARY OF THE INVENTION

The handpiece of the invention comprises the following characteristic features known from document US 2002/0120315: it includes a first and a second window and cooling means for the first window, said first and second windows being arranged opposite one another and separated by a gas-filled space, and being suitable for transmitting a light beam, said first window being intended to be applied in contact with the skin during treatment.

In a characteristic manner according to the invention, the handpiece includes means for heating the gas between the two windows.

Preferably, but optionally according to the invention, the handpiece includes the following additional technical characteristics, taken in isolation or in combination:

the space (E) between the two windows is closed;
the gas between the two windows is air;
the gas between the two windows is nitrogen or a mixture of air and nitrogen;

said heating means enable the gas to be held and maintained between the two windows at a temperature higher than the dew-point temperature of the gas;
said heating means enable the second window to be heated;
said heating means enable the second window to be held and maintained above the minimum temperature (T2);
said minimum temperature (T2) is higher than 15° C.;
the first cooling means enable the first window to be cooled and maintained at a temperature (T1) lower than 8° C.;
the first cooling means and the heating means include a Peltier-effect thermoelectric cooler, and include a warm face and a cold face, the cold face enabling the first window to be cooled and the warm face enabling the second window to be heated;
the first cooling means and the heating means are fully or partly housed in the space (E) between the two windows;
the Peltier-effect thermoelectric cooler is housed between the two windows;
the Peltier-effect thermoelectric cooler is in the shape of a ring;
the heating means include a thermal transfer element, which is positioned in contact with the interior face of the second window and with the warm face of the Peltier-effect thermoelectric cooler, and which enables part of the heat supplied by the warm face of the Peltier-effect thermoelectric cooler to be transferred to the second window, and part of the heat supplied by the warm face of the Peltier-effect thermoelectric cooler to be evacuated to the outside of the space (E);
the handpiece includes second means for cooling the thermal transfer element;
the second cooling means include a Peltier-effect thermoelectric cooler and means for dissipating the heat from the warm face of this thermoelectric cooler;
the heating means are positioned outside of the space (E) between the two windows;
the heating means include a heat source and a thermal transfer element (S"), thermally linking the heat source to the second window;
this thermal transfer element (S") enables the exterior face of the second window (2) to be heated by conduction;
the handpiece includes means for dissipating the heat from the heat source;
the first cooling means include a thermal transfer element (S') in contact with the first window and a cold source for the cooling of this element (S');
the handpiece comprises a Peltier-effect thermoelectric cooler, the cold face of which constitutes said cold source, and the warm face of which constitutes said heat source;
the thermal transfer elements (S') and (S") are separated by a thermal insulator;
the handpiece includes a thermal insulator interposed between the internal face of the second window and the first cooling means.

A further object of the invention is a device for treating the skin by irradiation by means of a light beam. In a characteristic manner according to the invention, the device includes a handpiece as previously described, a light source, and optical means for producing from the light source a light beam passing through the first and second windows.

More particularly, the light source is a laser source. The invention is nevertheless not limited to this particular type of light source, but can be extended to include any light source supplying a radiation enabling the skin of a patient to be treated. The light source can for instance include one or several high-power electroluminescent diodes. This light source can be an integral part of the handpiece or be separate from the handpiece being linked to the handpiece by an optical fibre.

In a particular embodiment of the invention, the device includes image acquisition means, and the two windows of the handpiece are positioned in the field of vision of said image acquisition means.

DETAILED DESCRIPTION

Figure 1:
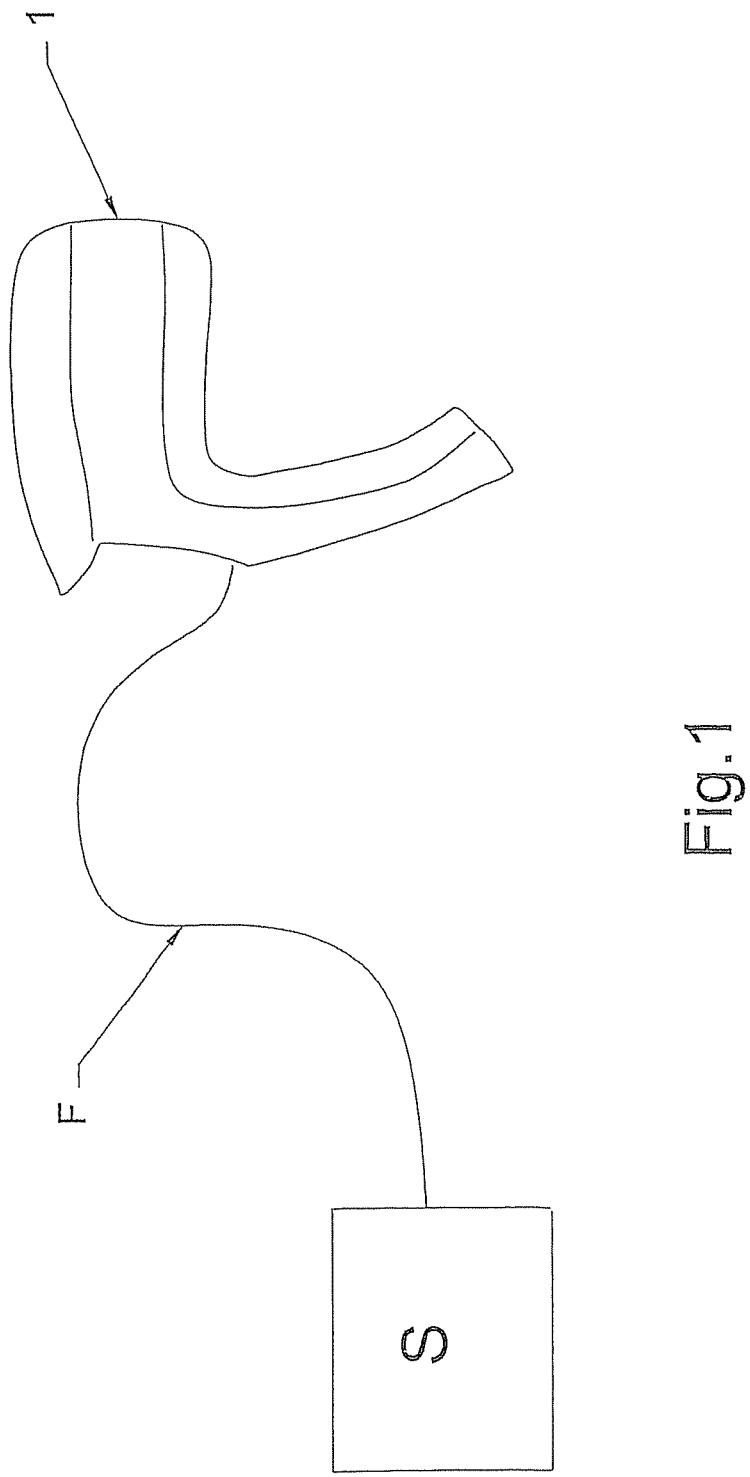
FIG. 1 is a general representation of a handpiece according to the invention linked to a light energy source by an optical fibre.

FIG. 1 shows a cooled handpiece according to the invention. This handpiece is linked by an optical fibre F to a light energy source S, preferably a laser source, and is used for treating the skin of a patient by irradiation, in particular for a vascular, pigmentary or depilatory treatment. In a further embodiment, the light source can also be integrated with the handpiece, and it is not necessary in this case to implement an optical fibre.

To lessen the pain felt by the patient, it is important to cool the skin of the patient at the level of the radiation zone. For this reason, this handpiece includes a cooling device, two embodiments of which are detailed hereinafter. Also, this handpiece has the advantage that the appearance of condensation in the handpiece is limited, even avoided, as a result of this cooling. The formation of condensation drops on the path of the therapeutic light beam is thus advantageously reduced and, if necessary, in the field of vision of the camera of the handpiece, when the piece includes a camera for carrying out the acquisition of an image of the treated zone.

Figure 2:
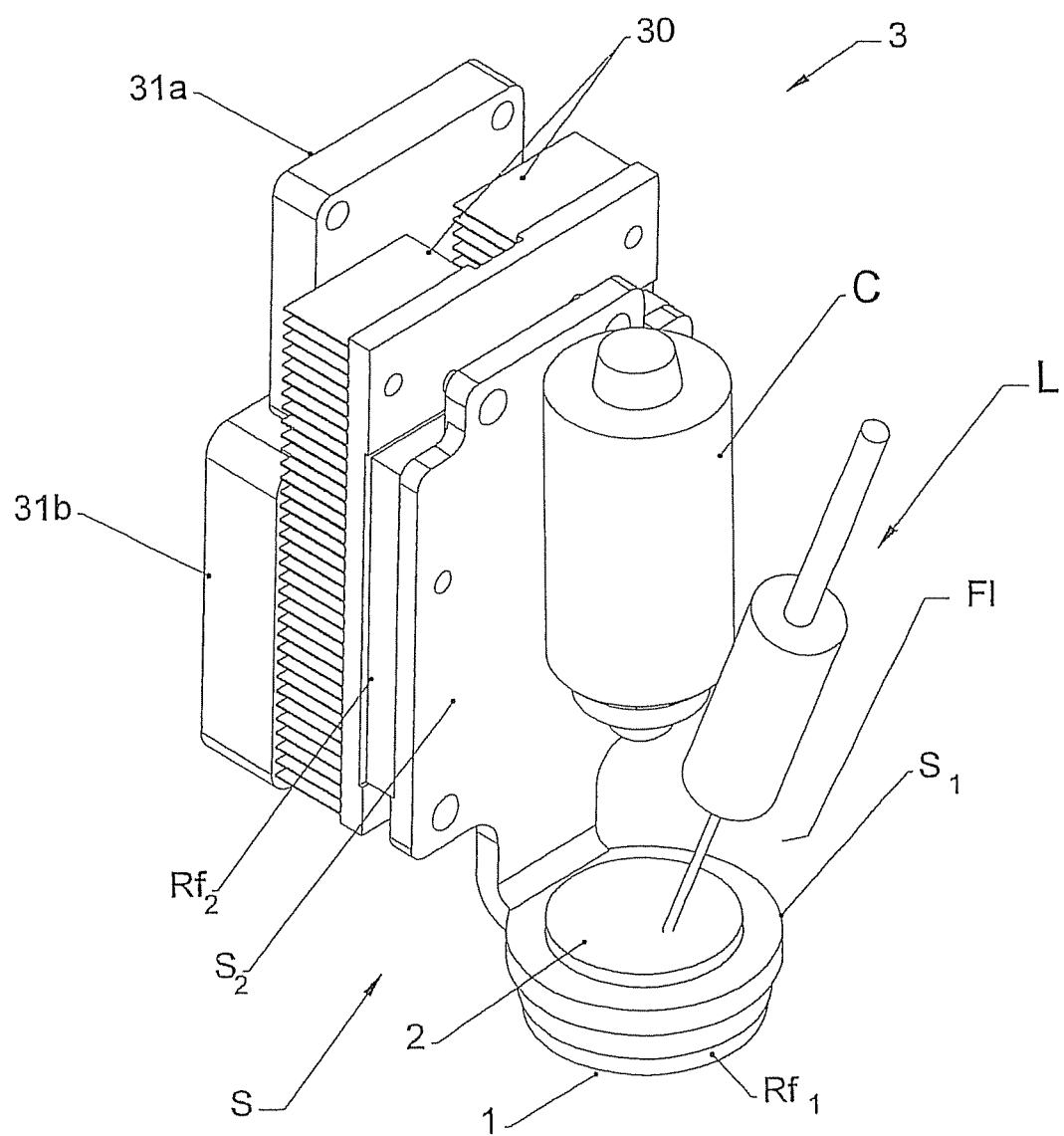
FIG. 2 is a perspective representation of a cooling device of a handpiece according to a first embodiment of the invention.
Figure 4:
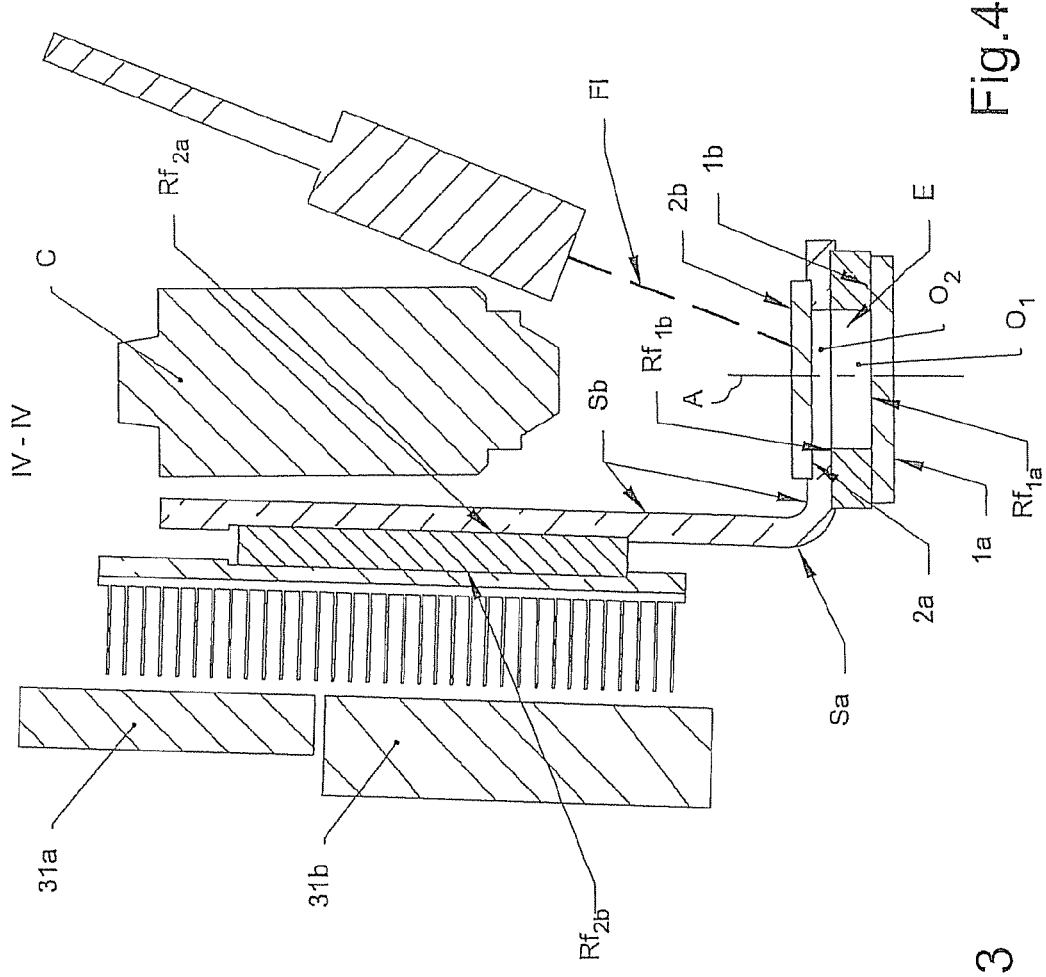
FIG. 4 is a longitudinal section view of the cooling device of FIGS. 2 and 3.
Figure 3:
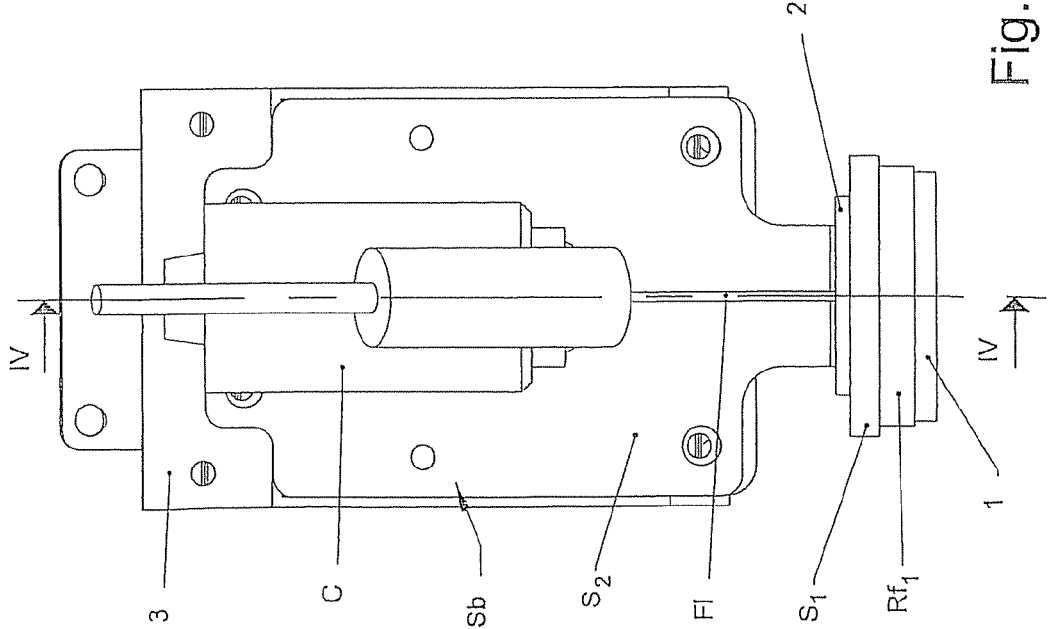
FIG. 3 is a side view of the cooling device of FIG. 2.

FIGS. 2 to 4 show in a simplified manner a handpiece according to a first embodiment of the invention provided with a first cooling means enabling the window to be cooled upon contact with the skin of the patient, and provided with a second cooling means and heating means. These drawings also show optical means L emitting a light beam Fl as well as an image acquisition device, for instance a camera C, for visualising on a screen (not represented) the treatment zone radiated by the light beam Fl. The optical means L comprise for instance a plurality of lenses and mirrors (not represented) enabling the light beam Fl to be focused.

The handpiece of this first embodiment comprises a first window 1, through which a light beam Fl is intended to pass. The material of this first window 1 is thus chosen so as to be transparent for the wavelength or for a range of wavelengths of the light beam Fl. For instance, a window 1 out of sapphire may be chosen, transparent for a range of wavelengths extending from 400 nm to 3000 nm, since this material also features good thermal conductivity. The window 1 is the element that is in direct contact with the skin of the patient during a treatment carried out with the handpiece. To this effect, it is convenient preferably to cool the window 1 prior to, and during the use of the handpiece on the skin of a patient.

The window 1 comprises a first exterior face 1a destined to be in contact with the skin and a second interior face 1b opposite said first face 1a.

A first cooling means, for instance a thermoelectric Peltier-effect cooler $Rf_1$ is fastened to the face 1b of the first window 1 and is intended to cool said window 1. Such a cooler is commonly designed as a TEC (thermoelectric cooler) by the person skilled in the art. In an advantageous manner according to the invention, the cooler $Rf_1$ is a ring comprising an opening $O_1$ enabling the light beam Fl to pass through and the treatment zone to be visualised by means of the camera C.

The ring of the cooler $Rf_1$ comprises a first face $Rf_{1a}$ fastened to the face 1b of the window 1 and a second face $Rf_{1b}$ opposite said first face $Rf_{1a}$. Since the ring is a TEC intended to cool the sapphire window 1, its face $Rf_{1a}$ constitutes the cold face of the cooling means $Rf_1$ and its face $R_{1b}$ constitutes its warm face.

The warm face $Rf_{1b}$ of the cooler $Rf_1$ is also fastened to a thermal transfer element, in particular a window support S, comprising a face Sa and a face Sb opposite said face Sa. The support S is for instance made out of copper and is arranged in such a manner that the ring of the cooler $Rf_1$ is sandwiched between, on the one hand, the face 1b of the window 1 and, on the other hand, the face Sa of the support S. More precisely, the face Sa of the support S is fastened to the face $Rf_{1b}$ of the cooling means $Rf_1$.

The support S essentially has the shape of an L presenting a base $S_1$ and a wall $S_2$ essentially perpendicular to said base $S_1$. The base $S_1$, on which the cooling means $Rf_1$ are fastened, comprises a traversing opening $O_2$ axially aligned according to an axis A with the opening $O_1$ of the ring of the cooling means $Rf_1$. This opening advantageously enables the light beam Fl to pass through and the treatment zone to be visualised by means of the camera C.

In addition, a second window 2 transparent for the wavelength or the range of wavelengths of the beam Fl is fastened on the base $S_1$. This second window 2 is for instance made out of glass. This second window 2 comprises an interior face 2a and an exterior face 2b opposite said face 2a. More particularly, the face 2a of the window 2 is fastened to the face Sb of the base $S_1$ of the support of the window S. Moreover, the second window 2, like the base $S_1$ of the support S, the ring of the cooler $Rf_1$ and the sapphire window 1, enables the light beam Fl to pass through and the treatment zone to be visualised with the help of the camera C.

Furthermore, the cavity defined by the two windows 1 and 2 by the cooler ring $Rf_1$ and by the support S constitutes a space E, preferably hermetically sealed, and containing a gas, for instance at atmospheric pressure. Most often this gas will be air. However, when the space E is hermetically sealed, one can envisage filling this space E with any other gas, such as nitrogen or a mixture of air and nitrogen.

In an advantageous manner according to the invention, the cooling means $Rf_1$ acts as a heat pump by taking up calories at a cold source (the window 1) to bring them to a heat source (the support S). Thus, the window 1 becomes cool, while the support S becomes warmer, as does the window 3, by conduction, which enables the temperature of the window 1 to be lowered upon contact with the skin of the patient and the gas enclosed within the space E to be heated. For this reason, the previously mentioned heating means comprise, in this embodiment of the invention, the warm face $Rf_{1b}$ of the cooler $Rf_1$ and the support S. Said heating means are intended to bring the temperature of the space E to a temperature higher than the condensation temperature of the gas enclosed in the space E. In the particular example of the first embodiment, the heating means enable the space E to be reheated by a heating of the interior face 2a of the second window 2.

Furthermore, the wall $S_2$ of the support S is linked to a second cooling means, for instance a Peltier-effect thermoelectric cooler $Rf_2$ (TEC). This cooler $Rf_2$ is in the form of a rectangular plate, which prevents an excessively high increase in the temperature of the support S. In effect, to avoid the appearance of condensation, it is advantageous to maintain the gas enclosed in the space E at a temperature that is higher than the dew-point temperature of the gas contained in the space E. In a known manner, this dew-point temperature depends in particular on the pressure of the gas, and the relative humidity level (RH) of the gas. For air at atmospheric pressure and featuring a maximum relative humidity level (RH) of 50%, this dew-point temperature is always lower than 15° C. When the gas is air, the gas is preferably maintained at a minimum temperature that is higher than 15° C. Nevertheless, it is preferable to avoid an excessively high increase in the temperature of the second window 2 above this limit (15° C. in the case of air at atmospheric pressure), in order not to reduce the capability of the cooling of the first window 1.

More precisely, this cooler $Rf_2$ comprises a first face $Rf_{2a}$, fastened against the face Sa of the wall $S_2$ of the support S, and a second face $Rf_{2b}$ opposite said first face $Rf_{2a}$.

Since the cooler $Rf_2$ is a TEC intended to cool the support S, its face $Rf_{2a}$ constitutes the cold face of said second cooling means $Rf_{2b}$ and its face $Rf_{2b}$ constitutes its warm face.

Advantageously, and to improve the evacuation of the heat of the support S and to improve the capability of the cooling means $Rf_1$ and $Rf_2$, the second cooling means $Rf_2$ are associated with heat dissipation means comprising a radiator 3, for instance out of copper, and fins 30 associated with two ventilators 31a, 31b to speed up the evacuation of the heat.

Figure 8:
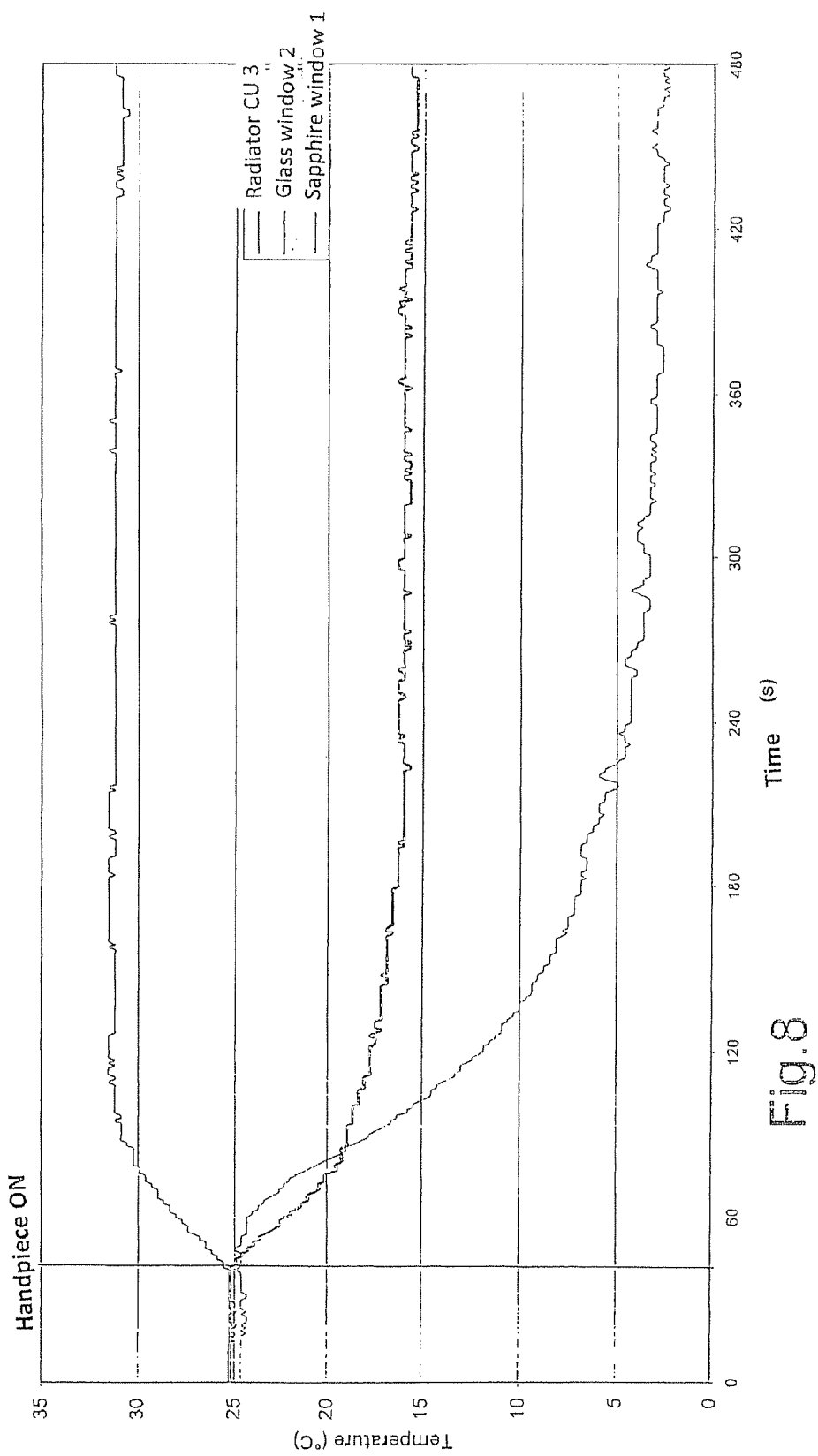
FIG. 8 is a graph representing the evolution of the temperatures in the handpiece in relation to time for the first embodiment of the invention.

In a preferred method of use of the handpiece shown in FIG. 8, the cooler $Rf_1$ operates in order rapidly to bring and maintain the temperature (T1) of the sapphire window 1 to a temperature between 4° C. and 8° C. and the cooler $Rf_2$ enables the temperature of the support S to be maintained at a temperature between 15° C. and 20° C. Since the support S is a thermal transfer element linked to the warm face $Rf_{1b}$ of the cooler $Rf_1$, the temperature (T2) of the glass window 2 is also rapidly brought to and maintained at a temperature between 15° C. and 20° C.

In addition, since the Peltier effect results in the transfer of the heat from a cold source to a heat source, the temperature of the radiator 3 increases to between 30° C. and 35° C.

The objective aimed at by the present invention is to prevent the appearance of condensation on the windows 1 and 2. This objective is achieved by bringing and maintaining the temperature of the gas contained in the space E at a temperature higher than the condensation temperature of the gas.

The simultaneous use of two separate cooling means enables a better efficiency and better control of the temperatures to be achieved. Indeed, while the warm face $Rf_{1b}$ of the cooler $Rf_1$ tends to heat the support S through heat transfer from the sapphire window 1 towards said support S, the second cooling means $Rf_2$ contributes to maintaining the temperature of the window 2 at between 15° C. and 20° C. by simultaneously cooling said support S.

A handpiece as described above can be obtained by means of a standard (TEC) cooler $Rf_2$ measuring 40×40×4 mm with a power of 75 W and a ring cooler $Rf_1$ with a 26 mm external diameter, a 14 mm internal diameter and a power of 6.6 W.

The results obtained with these parameters can be seen on the graph of FIG. 8 showing the evolution of the temperature of the radiator 3 and the windows 1, 2 in relation to time (in seconds).

Figure 5:
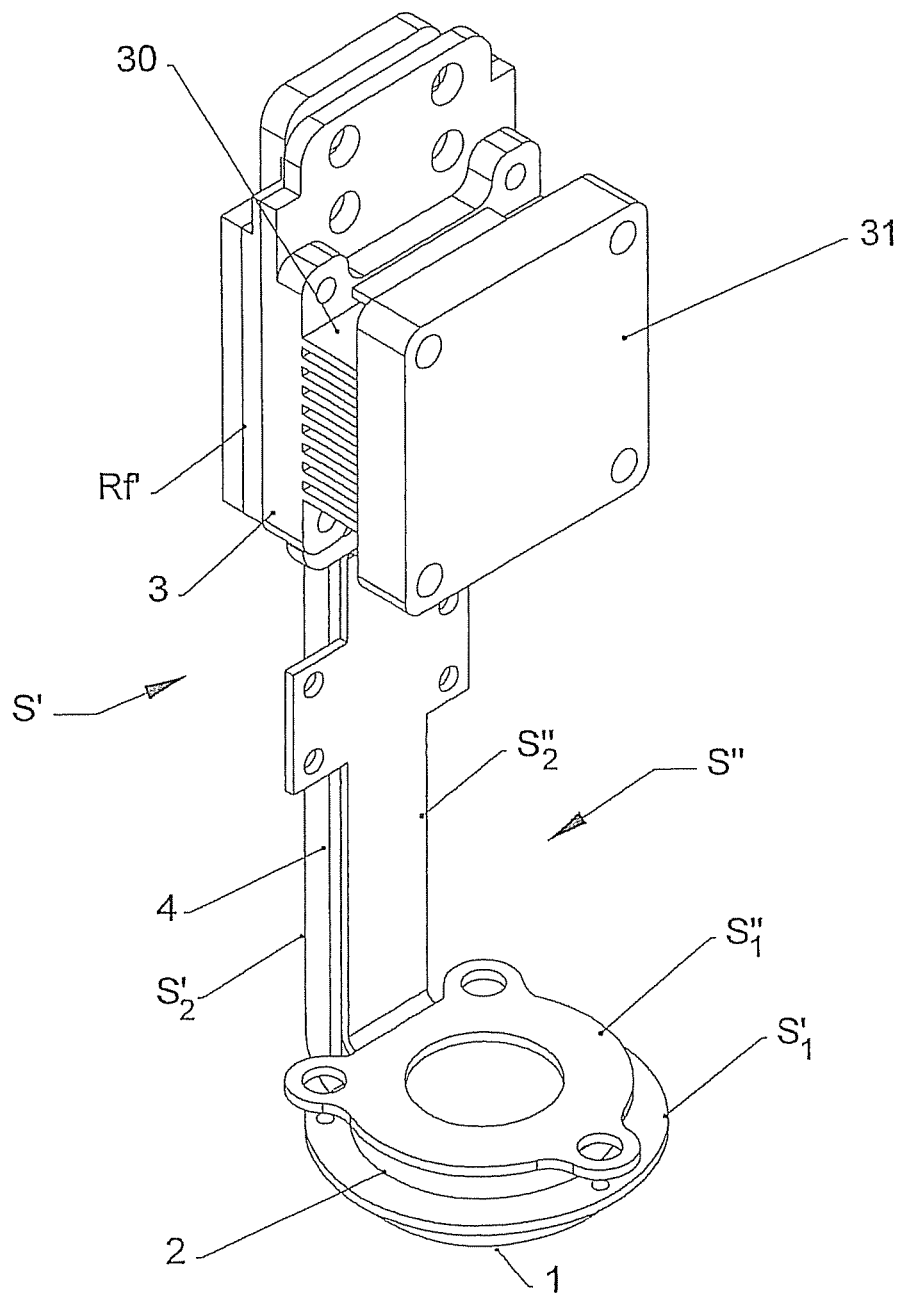
FIG. 5 is a perspective representation of a cooling device of a handpiece according to a second embodiment of the invention.
Figure 7:
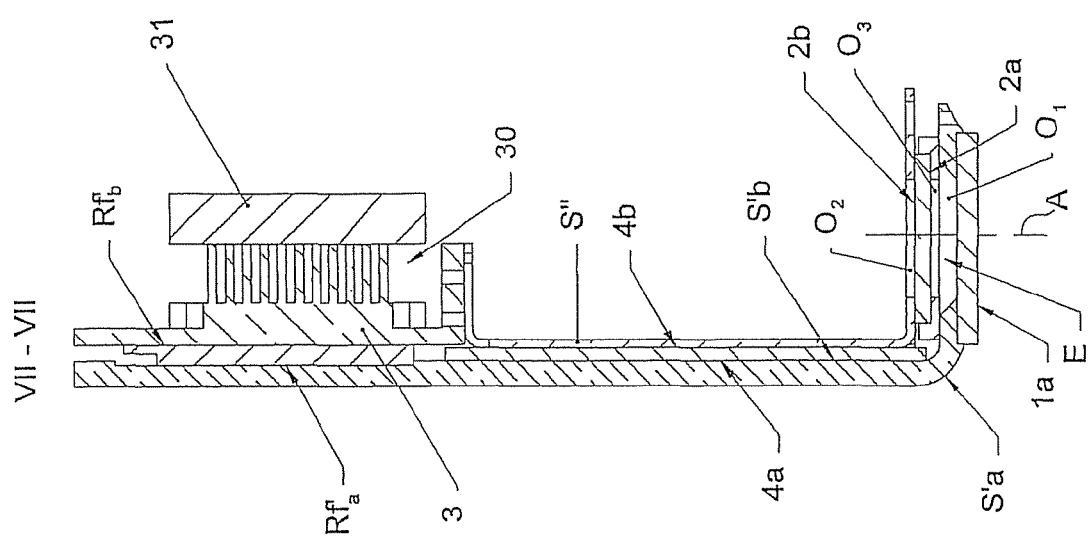
FIG. 7 is a longitudinal section view of the cooling device of FIGS. 5 and 6.
Figure 6:
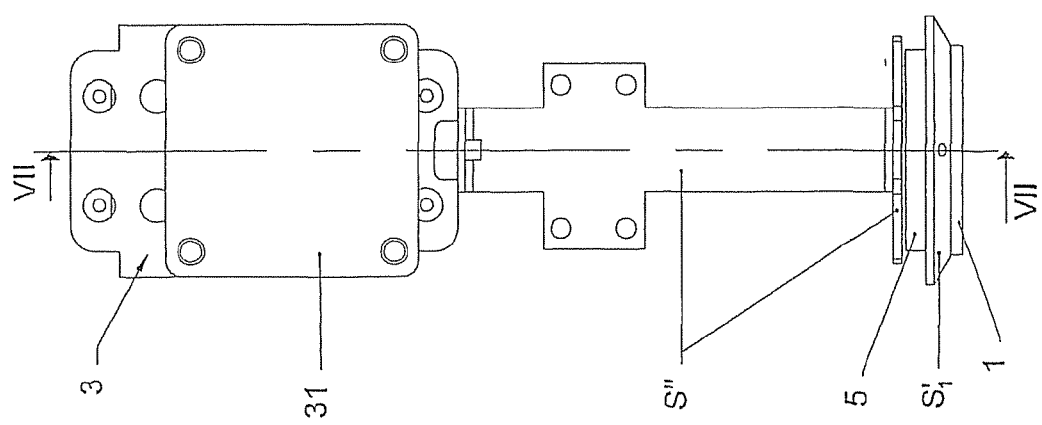
FIG. 6 is a side view of the cooling device of FIG. 5.

FIGS. 5 to 7 show a handpiece according to a second embodiment of the invention equipped with first cooling means of the first window 1 and heating means of the second window 2.

More particularly, in this second embodiment of the invention, the first cooling means comprise for instance a Peltier-effect thermoelectric cooler Rf' and are associated with a first thermal transfer element, in particular a window support S' for the window 1, and with a second thermal transfer element, in particular a window support S" for the window 2, the two supports being for instance made out of copper.

The support S' comprises an internal face S'a, on which is fastened the first window 1 intended to be cooled, and an exterior face S'b opposite said face S'a. More particularly, the support S' essentially has an L shape featuring a base $S'_1$, comprising as in the first embodiment an opening $O_1$, and a wall $S'_2$ essentially perpendicular to said base $S'_1$. The exterior face 1b of the first window 1 is fastened to the interior face S'a of the base $S'_1$ of the support S'.

Furthermore, the cooler Rf' comprises a first face $Rf'_a$, via which it is fastened to the face S'b of the wall $S'_2$ of the support S', and a second face $Rf'_b$ opposite said first face $Rf'_a$.

Since the cooler Rf' is a TEC intended to cool the window 1 and to heat the window 2, the face Rf'r$_a$ fastened on the first support S' constitutes the cold face of the cooler Rf' and the face $Rf'_b$ constitutes the warm face. For this reason, heat dissipation means comprising a radiator 3 with fins 30 associated to a ventilator 31 have been fastened to said warm face $Rf'_b$ of the cooler Rf' to evacuate the heat.

The support S" is intended to thermally link the radiator 3 to the window 2. Said support S" essentially has a U shape and comprises an opening $O_2$ enabling a light beam Fl to pass through and the treatment zone to be visualised by means of a camera.

The support S" is also linked to an insulating plate 4 comprising a first face 4a, via which it is fastened to the face S'b of the wall $S'_2$ of the support S', and a second face 4b, opposite said first face 4a, on which the second support S" is fastened. In this manner, the insulating plate 4 enables the support S' that is intended to be cooled to be thermally insulated from the support S" that is intended to be heated.

In this embodiment, the second window 2 is fastened via its exterior face 2b to the second support S" in such a manner that it is heated by said support S". In addition, the window 2 is axially aligned along the axis A with the opening $O_2$.

The window support S", on which the second window 2 is fastened, is in direct contact with the radiator 3, which is in turn in contact with the warm face $RF'_b$ of the cooler Rf'. To this effect, when the handpiece is in operation, the second window 2 and the window support S" are heated, by conduction, by the warm face $Rf'_b$ of the cooler Rf' and by the radiator 3, while the first window 1 and the first support S' are cooled. For this reason, the insulating plate 4 has been advantageously positioned between the supports S' and S" to insulate the cooled support S' from the heated support S".

Furthermore, the handpiece of the second embodiment of the invention comprises an insulating disc 5 sandwiched between the face 2a of the second window 2 and the face S'a of the base $S'_1$ of the first window support S'. This insulating disc 5 enables the window 2, which is heated, to be thermally insulated from the window 1 and the support S', which are cooled. The disc 5 also comprises an opening $O_3$, axially aligned along the axis A, enabling a light beam Fl to pass through and the treatment zone to be visualised by a camera.

In addition, the openings $O_1$ and $O_3$ defined by the windows 1 and 2 constitute, as in the first embodiment, a space E, preferably hermetically sealed, containing air or any other gas, for instance nitrogen or a mixture of air and nitrogen.

Advantageously according to this second embodiment of the invention, the cooling of the first window 1 is achieved thanks to the support S' and the cooler Rf' and the heating of the second window 2 is achieved thanks to the warm face $Rf'_b$ of the cooler Rf', the radiator 3 and the support S". Indeed, in this embodiment, the window 1 is cooled by the intermediary of the first window support S' and the cold face $Rf'_a$ of the first cooling means Rf', while the window 2 is heated by the intermediary of the warm face $Rf'_b$ of the cooler Rf', the radiator 3 and the second window support S".

The invention is not limited to the embodiment of the annexed drawings. Other embodiments available to the person skilled in the art and covered by the annexed claims can be envisaged, without however departing from the context of the invention. For instance, the cooling means are not limited to the use of a thermoelectric cooler, any other cooling means known to the person skilled in the art also being suitable for use in a handpiece covered by the annexed claims.

In the same manner, the heating means are not limited to the use of a thermal transfer element in contact with the warm face of the cooler, but can be replaced by any equivalent means enabling the second window 2 to be heated. More generally still, the heating means of the second window 2 can be replaced by any means enabling the air contained in the space E between the two windows 1 and 2 to be heated, the invention not being limited to a heating of this gas through the heating of the second window.

In the embodiments in the annexed drawings, the handpiece includes an image acquisition means (camera) enabling the operator of the handpiece to visualise the treatment zone. Nevertheless, in a simpler embodiment, the handpiece can be without image acquisition means.

The invention claimed is:

1. A handpiece for treating the skin by irradiation by means of a light beam, said handpiece including a first and a second window and first cooling means of the first window, said first and second window being arranged opposite one another and separated by a space containing a gas, and being suitable for letting a light beam pass through, said first window being intended to make contact with the skin during treatment, said handpiece further comprising heating means for heating the gas between the two windows, wherein said heating means comprises a heat source and a first solid thermal transfer element, wherein said first solid thermal transfer element is in contact with the second window and is thermally linking the heat source to the second window in order to heat the second window.

2. The handpiece according to claim 1, wherein the space between the two windows is closed.

3. The handpiece according to claim 1, wherein the gas between the two windows is air.

4. The handpiece according to claim 1, wherein the gas between the two windows is nitrogen or a mixture of air and nitrogen.

5. The handpiece according to claim 1, wherein said heating means enable the gas to be held and maintained between the two windows at a temperature higher than the dew-point temperature of the gas.

6. The handpiece according to claim 1, wherein said heating means are arranged in such a manner as to enable the second window to be heated.

7. The handpiece according to claim 6, wherein the heating means enable the second window to be held and maintained above a minimum temperature.

8. The handpiece according to claim 7, wherein the minimum temperature is higher than 15° C.

9. The handpiece according to claim 1, wherein the first cooling means enable the first window to be cooled and maintained at a temperature lower than 8° C.

10. The handpiece according to claim 1, wherein the first cooling means and the heating means include a Peltier-effect thermoelectric cooler and include a warm face and a cold face, the cold face enabling the first window to be cooled and the warm face enabling the second window to be heated.

11. The handpiece according to claim 1, wherein the first cooling means and the heating means are fully or partly housed in the space between the two windows.

12. The handpiece according to claim 10, wherein the first cooling means and the heating means are fully or partly housed in the space between the two windows and the Peltier-effect thermoelectric cooler is housed between the two windows.

13. The handpiece according to claim 12, wherein the Peltier-effect thermoelectric cooler has the shape of a ring.

14. The handpiece according to claim 1, wherein the heating means and the first cooling means comprise a Peltier-effect thermoelectric cooler having a cold face for cooling the first window and a warm face which constitutes said heat source and is in contact with the first solid thermal transfer element.

15. The handpiece according to claim 14, wherein it includes a second cooling means for cooling the first solid thermal transfer element.

16. The handpiece according to claim 15, wherein the second cooling means include a Peltier-effect thermoelectric cooler and means for dissipating the heat from the warm face of this thermoelectric cooler.

17. The handpiece according to claim 1, wherein the heating means are positioned outside of the space between the two windows.

18. The handpiece according to claim 1 wherein the first solid thermal transfer element is enabling the exterior surface of the second window to be heated by conduction.

19. The handpiece according to claim 1, wherein it includes means for dissipating the heat from the heat source.

20. The handpiece according to claim 1, wherein the first cooling means include a second solid thermal transfer element in contact with the first window and a cold source for the cooling of the second solid thermal transfer element.

21. The handpiece according to claim 1, wherein the first cooling means include a second solid thermal transfer element in contact with the first window and a cold source for the cooling of the second solid thermal transfer element and it includes a Peltier-effect thermoelectric cooler, the cold face of which constitutes said cold source, and the warm face of which constitutes said heat source.

22. The handpiece according to claim 1, wherein the first cooling means include a second solid thermal transfer element in contact with the first window and a cold source for the cooling of the second solid thermal transfer element and the first and second solid thermal transfer elements are separated by a thermal insulator.

23. The handpiece according to claim 1, wherein it incudes a thermal insulator arranged between the internal face of the second window and the first cooling means.

24. A device for treating the skin by irradiation by means of a light beam, wherein it includes a handpiece in accordance with claim 1, a light source and optical means for producing from the light source a light beam passing through the first and second windows.

25. The device according to claim 24, wherein the light source is a laser source.

26. The device according to claim 24, wherein it includes image acquisition means, and in that the two windows are positioned in the field of vision of said image acquisition means.

27. The handpiece according to claim 1, wherein the first solid thermal transfer element comprises an opening for enabling the light beam to pass through.

28. The handpiece according to claim 1, wherein the first solid thermal transfer element is in contact with an interior surface of the second window.

29. The handpiece according to claim 1, wherein the first solid thermal transfer element is in contact with an exterior surface of the second window.

30. The handpiece according to claim 10, wherein the warm face of the Peltier-effect thermoelectric cooler is in contact with the first solid thermal transfer element.

31. The handpiece according to claim 30 wherein the first solid thermal transfer element enables part of the heat supplied by the warm face of the of the Peltier-effect thermoelectric cooler to be transferred to the second window.

32. The handpiece according to claim 31 wherein the first solid thermal transfer element enables part of the heat supplied by the warm face of the of the Peltier-effect thermoelectric cooler to be evacuated outside the space between first and second windows.

33. The handpiece according to claim 1 wherein a Peltier-effect thermoelectric cooler is positioned between the first and second window and comprises an opening for enabling the light beam to pass through.

34. The handpiece according to claim 1 wherein said first solid thermal transfer element is fastened to the second window.

35. The handpiece according to claim 1 wherein said first solid thermal transfer element comprises a thermally conductive plate.

36. The handpiece according to claim 1 wherein said first solid thermal transfer element is made of metal.

37. The handpiece according to claim 1 wherein said first solid thermal transfer element is made of copper.

* * * * *

UNITED STATES PATENT AND TRADEMARK OFFICE
CERTIFICATE OF CORRECTION

PATENT NO. : 8,585,688 B2
APPLICATION NO. : 12/672966
DATED : November 19, 2013
INVENTOR(S) : Zemmouri et al.

Page 1 of 1

It is certified that error appears in the above-identified patent and that said Letters Patent is hereby corrected as shown below:

Title page, column 2, item (57) abstract line 2, delete "(F1)" and insert --(FI)--.

Title page, column 2, item (57) abstract line 6, delete "(F1)" and insert --(FI)--.

In the Specification

Column 1, line 4, Delete "CROSS REFERENCE" and insert --CROSS-REFERENCE--.

Column 1, line 46, Delete "C" and insert --C.--.

Column 6, line 31, Delete "$Rf_{2b}$" and insert --$Rf_2$--.

Column 7, line 29, Delete "$Rf'r_a$" and insert --$Rf'_a$--.

Column 7, line 53, Delete "$RF'_b$" and insert --$Rf'_b$--.

In the Claims

Column 10, claim 32, line 38, after "face", delete "of the".

Signed and Sealed this
Seventeenth Day of March, 2015

Michelle K. Lee
*Director of the United States Patent and Trademark Office*